United States Patent
Köhler et al.

(10) Patent No.: US 6,426,992 B1
(45) Date of Patent: Jul. 30, 2002

(54) COMPUTED TOMOGRAPHY APPARATUS INVOLVING A CONICAL RADIATION BEAM AND A HELICAL RELATIVE MOTION

(75) Inventors: Thomas Köhler, Norderstedt; Roland Proksa, Hamburg, both of (DE)

(73) Assignee: Koninklijke Philips Electronics, N.V., Eindhoven (NL)

(*) Notice: Subject to any disclaimer, the term of this patent is extended or adjusted under 35 U.S.C. 154(b) by 0 days.

(21) Appl. No.: 09/921,505

(22) Filed: Aug. 2, 2001

(30) Foreign Application Priority Data

Aug. 5, 2000 (DE) .......................... 100 38 328

(51) Int. Cl.[7] .................................. A61B 6/03
(52) U.S. Cl. .................... 378/19; 378/15; 378/901
(58) Field of Search ................ 378/4, 15, 19, 378/901

(56) References Cited

U.S. PATENT DOCUMENTS 6,269,141 B1 * 7/2001 Proksa et al. .................. 378/19

OTHER PUBLICATIONS

U.S. application No. 09/368,850, PHD 98,086 entitled "Computer tomography apparatus with a conical radiation beam and a helical scanning trajectory".

* cited by examiner

*Primary Examiner*—David V. Bruce
(74) *Attorney, Agent, or Firm*—John Vodopia

(57) ABSTRACT

The invention relates to a computed tomography apparatus whose radiation source emits a conical radiation beam and is capable of scanning the examination zone along a trajectory in the form of a helix. The detector unit that is connected to the radiation source consists of a plurality of spatially separated detector segments that are mutually offset in the axial direction and each of which is arranged in such a manner that a projection onto the helix covers at least two neighboring turns of the helix. A CT image having an improved and spatially more uniformly distributed signal-to-noise ratio can be reconstructed from the CT data acquired by means of such a detector unit.

6 Claims, 5 Drawing Sheets

Figure 1:
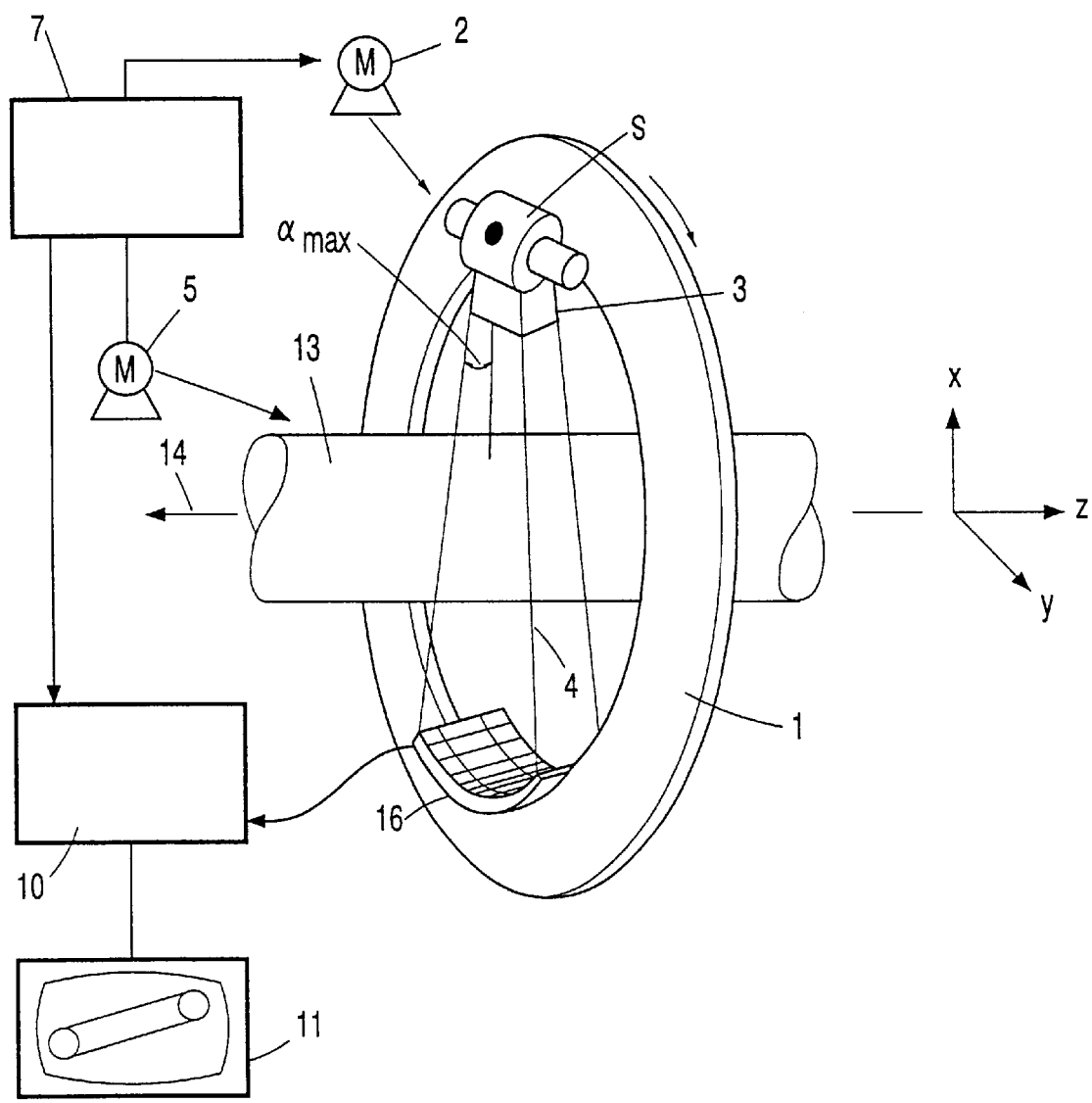

COMPUTED TOMOGRAPHY APPARATUS INVOLVING A CONICAL RADIATION BEAM AND A HELICAL RELATIVE MOTION

The invention relates to a computed tomography apparatus which includes a radiation source that emits a cone beam and moves along a helical path relative to an examination zone or an object present therein. The invention also relates to a detector unit that is suitable for use in such a computed tomography apparatus.

A computed tomography apparatus of this kind which is known from U.S. application Ser. No. 09/380,972 (PHQ 98.020) includes a detector unit which is connected to the radiation source and is struck by the cone beam after its passage through the examination zone, its shape being such that its outer edges that are mutually offset in the axial direction cover two neighboring turns of the helix. It can be demonstrated that the radiation source then projects the voxels in the examination zone onto the detector unit from an angular range of exactly 180°. A CT image of suitable quality can be reconstructed from the CT data (CT= Computed Tomography) thus acquired.

An even better image quality can be achieved by means of a computed tomography apparatus that is known from U.S. application Ser. No. 09/368,850 (PHD 98-086) in which the dimensions of the detector unit in the axial direction are such that the projection of the outer edges of the detector unit onto the helix encloses a path of (2n+1)p, where p corresponds to the axial offset of two neighboring turns of the helix. Each voxel in the examination zone is then projected onto the detector unit from an angular range of (2n+1).180°. As a result, the signal-to-noise ratio in the voxels is more uniformly distributed across the examination zone in comparison with the first mentioned computed tomography apparatus. Moreover, for the same relative speed between the radiation source and the examination zone the signal-to-noise ratio may be a factor of 2n+1 better than in the known computed tomography apparatus; however, to this end the dimensions of the detector unit must be a factor of 2n+1 larger in the axial direction.

However, the dimensions of given detector units cannot be increased at random in the axial direction. For example, when the detector unit is provided with semiconductor chips with detector elements arranged in the form of a matrix, the semiconductor chips must be concatenated in an arc-like manner in a plane perpendicular to the axis of rotation. Because electronic circuitry for processing the signals of the detector elements must be present on one of the four sides of a chip, only two chips can be arranged so as to be directly adjacent in the direction perpendicular to said plane, that is, in the axial direction, the electronic circuitry connected to the individual chips being situated each time on the sides of the chips that are remote from one another. However, because the dimensions of the chips are limited for production-technical reasons, the dimensions of the detector unit are also limited in the axial direction.

It is an object of the present invention to provide a computed tomography apparatus whose detector unit delivers, despite said limitations, CT data wherefrom CT images having an improved signal-to-noise ratio and a more attractive spatial distribution of the signal-to-noise ratio can be reconstructed.

This object is achieved in accordance with the invention by means of a computed tomography apparatus which includes a scanning unit which includes a radiation source and a detector unit which is connected thereto in order to detect a conical radiation beam, emitted by the radiation source, after its passage through an examination zone or an object present therein, a drive device for realizing a relative motion in the form of a helix, comprising a rotation about an axis of rotation and a displacement parallel to the axis of rotation, between the scanning unit and the examination zone or the object, the projection of the edges of the detector unit, being mutually offset in the axial direction, onto the helix including a path of (2n+1)p, where n is an integer $\geq 1$ and p corresponds to the axial offset of two neighboring turns of the helix, and the detector unit including a plurality of detector segments that are spatially separated from one another and are mutually offset in the axial direction, each of said detector segments being arranged and shaped in such a manner that its projection onto the helix covers at least two neighboring turns of the helix.

The invention utilizes symmetries in the data acquisition by means of the known computed tomography apparatus. When the projections of the outer edges of the detector unit that are mutually offset in the axial direction in such a computed tomography apparatus cover, for example, five times the distance between two neighboring turns of the helix, such a detector unit can imaginary be subdivided into five detector segments whose projection interconnects each time two neighboring turns of the helix.

The radiation source projects the voxels in the examination zone onto the central detector segment from an angular range of 180°. This data suffices to ensure complete reconstruction. On the other hand, reconstruction (with an enhanced image quality) is also possible on the basis of the CT data of the three inner detector segments onto which the voxels of the examination zone are projected from an angular range of 3 times 180°. Finally, reconstruction is also possible on the basis of the CT data of all five detector segments (onto which the voxels of the examination zone are projected from an angular range of 5 times 180°).

Because the reconstruction process used to process the CT data so as to form a (three-dimensional) CT image is linear, a respective complete CT image can be reconstructed each time from the CT data of the outer detector segments, the central detector segment and the detector segments that are situated therebetween. The invention utilizes this fact to omit individual detector segments or pairs of detector segments (for example, the two detector segments situated between the central detector segment and an outer detector segment). A CT image having a more favorable signal-to-noise ratio and a more uniform spatial distribution of this ratio in comparison with a CT image reconstructed exclusively from the CT data of the central detector segment can then still be reconstructed from the CT data of the detector segments then remaining.

The omission of these detector segments results in vacant areas between individual detector segments which can accommodate, for example the electronic circuitry for the individual detector segments or fixing points for the detector segments or anti-scatter grids arranged in front thereof.

Claim 2 discloses the simplest detector unit possible. However, such a detector unit gives rise to problems when a circular relative motion instead of a helical relative motion takes place between the examination zone and the radiation source. In that case the part of the examination zone that is situated in the plane between the two detector segments cannot be reconstructed without artefacts.

The embodiment of the invention that is disclosed in claim 3 is more attractive in this respect, be it that it requires at least three detector segments. A central slice that is free from said artefacts can be reconstructed, even in the case of a circular relative motion, by means of the detector segment which is situated in the plane of the radiation source.

Claim 4 discloses a preferred embodiment. The radiation load is thus reduced in a computed tomography apparatus used for medical applications.

The embodiment in accordance with claim 5 is suitable for the reconstruction of CT images for several energy ranges, the CT data required for this purpose being simultaneously acquired.

Claim 6 discloses a detector unit in accordance with the invention for a computed tomography apparatus.

Figure 2:
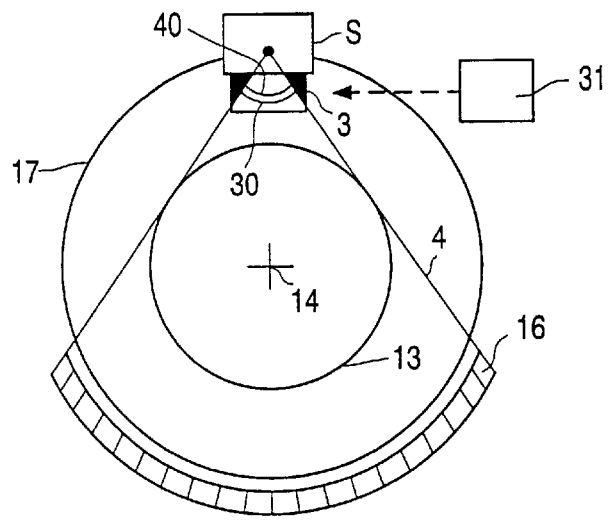
Figure 3:
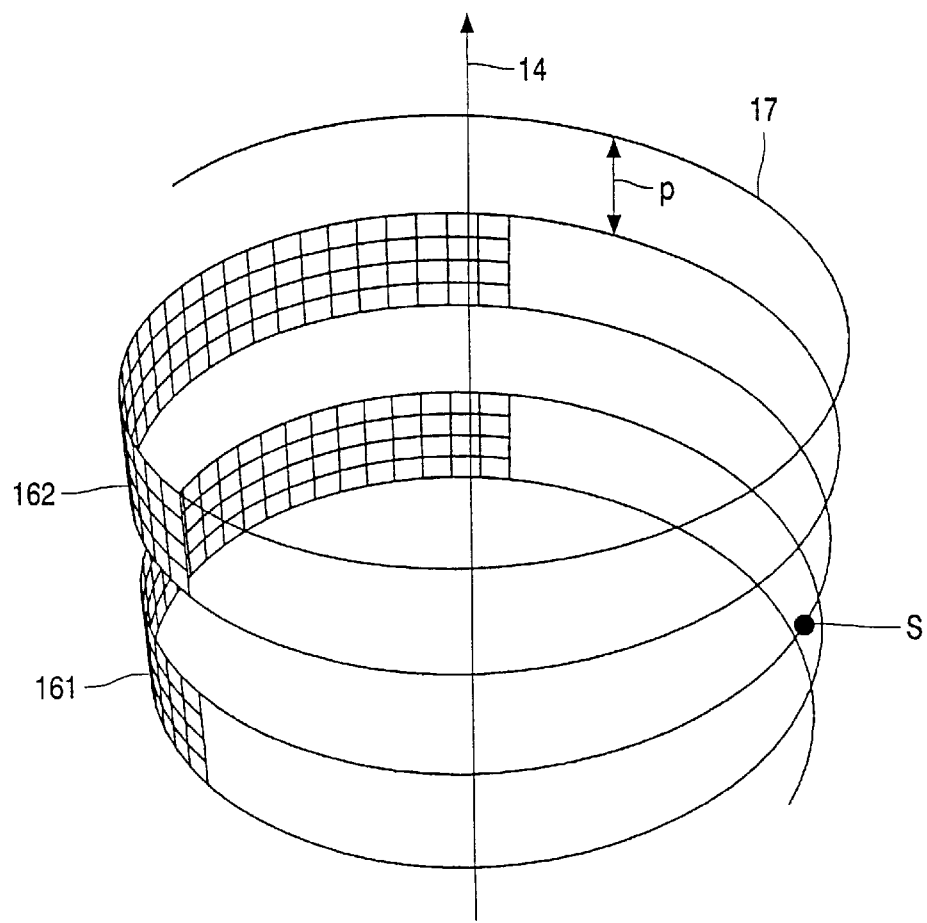
Figure 4:
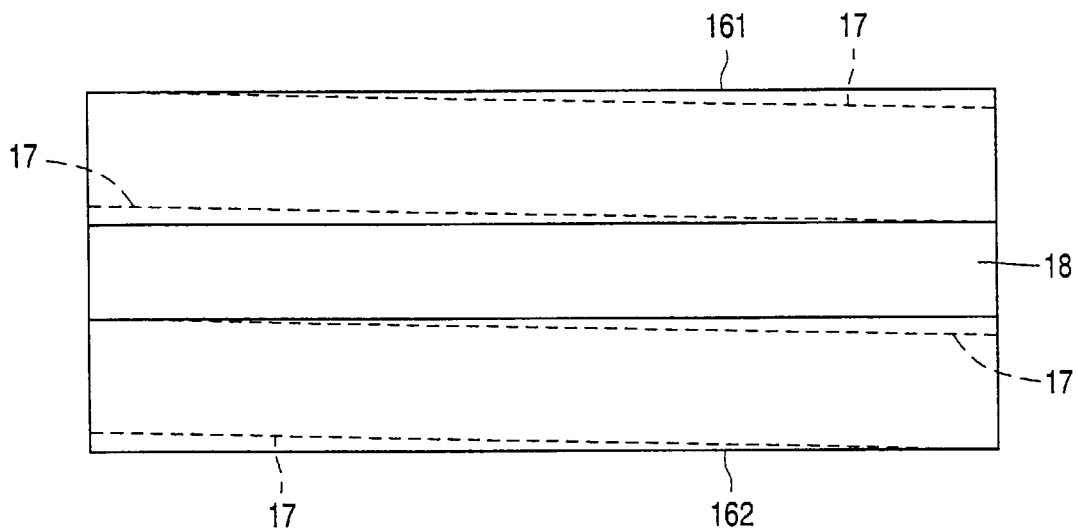
Figure 5:
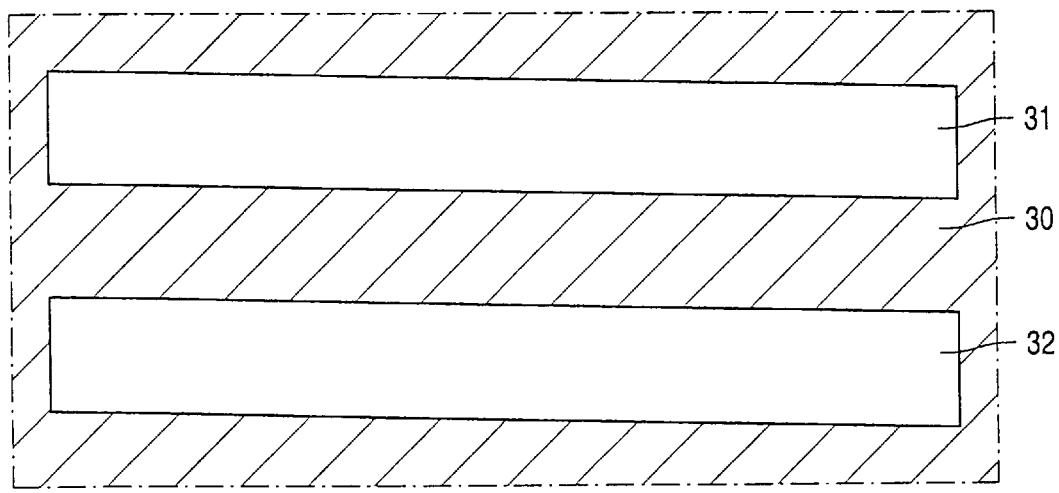
Figure 6:
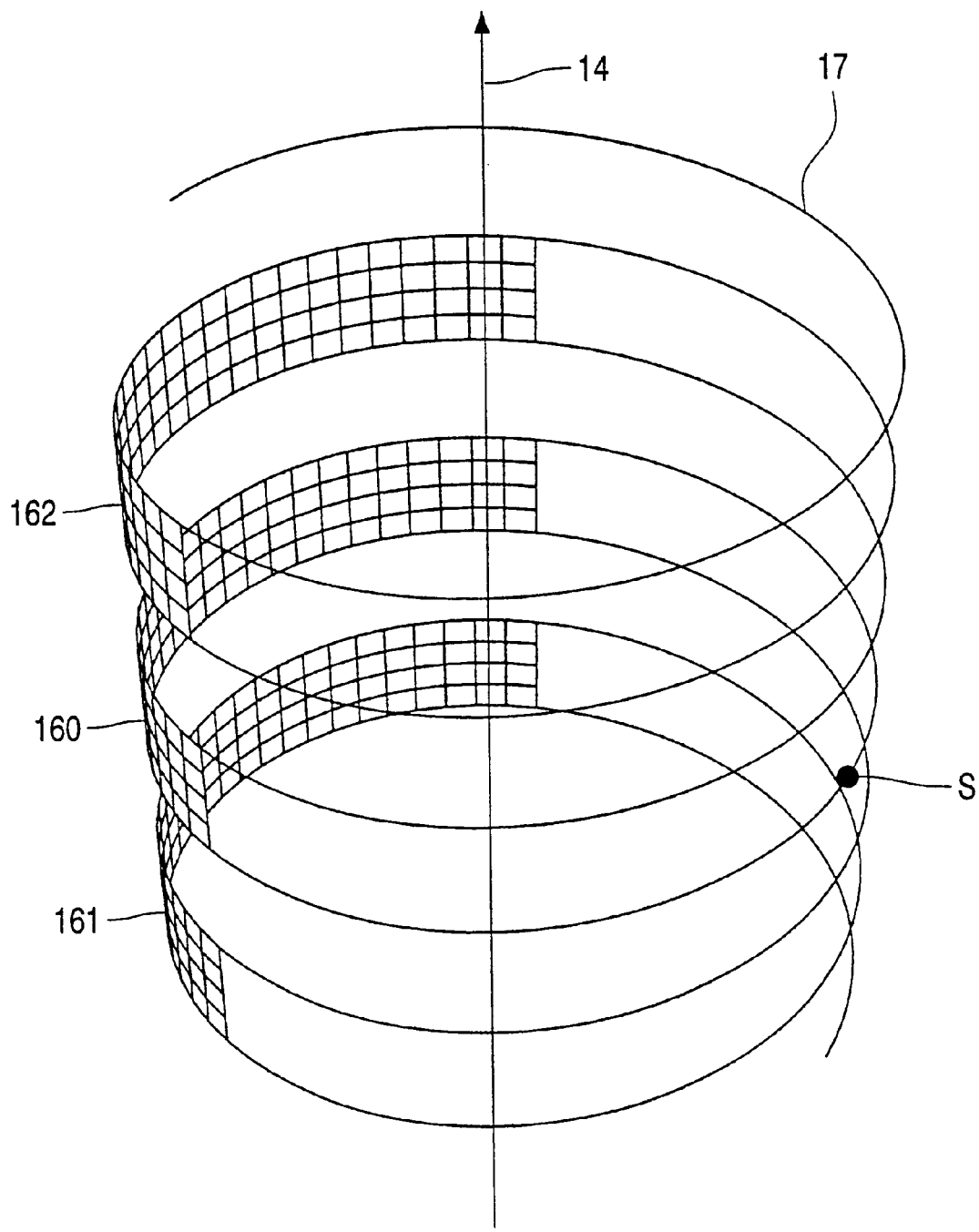
Figure 7:
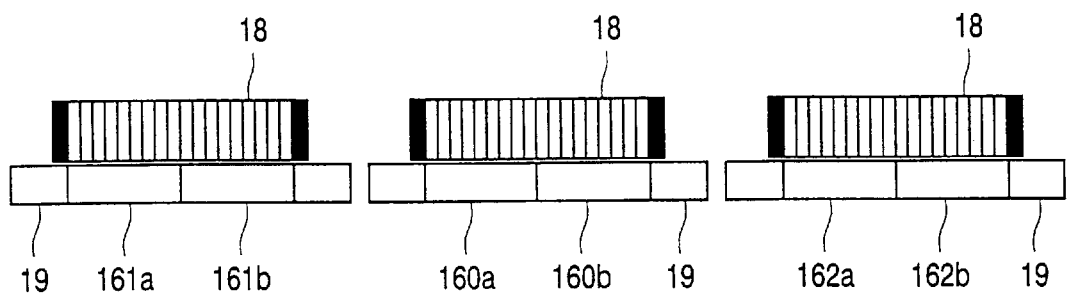
Figure 8A:
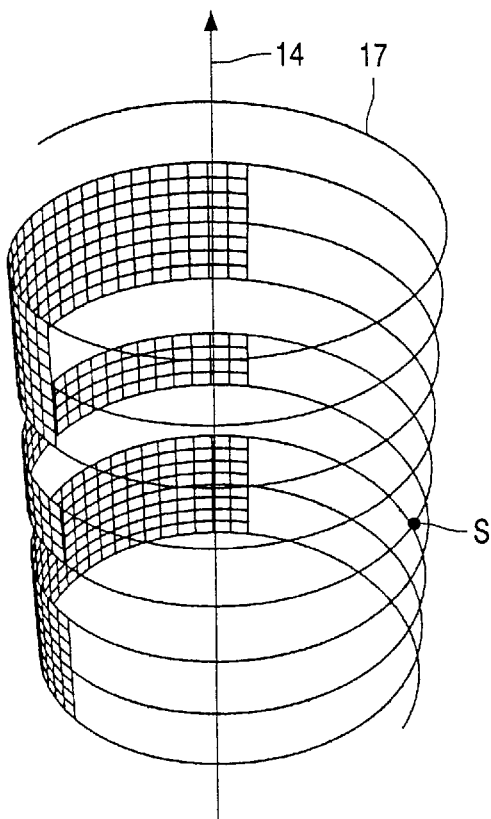
Figure 8B:
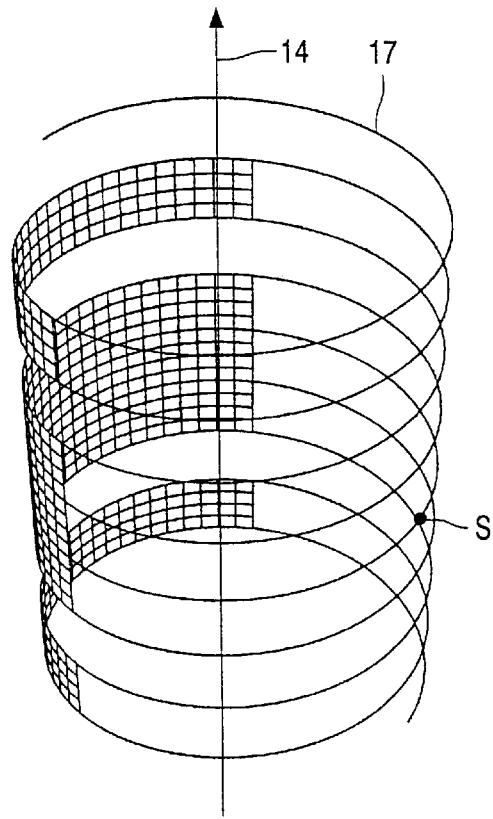

The invention will be described in detail hereinafter with reference to the drawing. Therein:

FIG. 1 is a diagrammatic view of a computed tomography apparatus in accordance with the invention, FIG. 2 is a simplified plan view of such a computed tomography apparatus, FIG. 3 shows the geometrical relations in such a computed tomography apparatus, FIG. 4 shows the development of a detector unit in accordance with the invention and the projection of the helical turns onto this unit, FIG. 5 shows an appropriate diaphragm 6 while FIG. 6 shows the geometrical relations in a second embodiment, FIG. 7 is a cross-sectional view of the latter embodiment in a plane containing the axis of rotation, and FIGS. 8a and 8b show the geometrical relations in two further embodiments of the invention.

FIG. 1 shows a computed tomography apparatus which includes a gantry 1 which is capable of rotation about an axis of rotation 14 that extends parallel to the z direction of the co-ordinate system shown in FIG. 1. To this end, the gantry is driven by a motor 2 at a preferably constant but adjustable angular speed. A radiation source S, for example an X-ray source, is connected to the gantry. The source is provided with a collimator device 3 which forms a conical radiation beam 4 from the radiation produced by the radiation source S, that is, a radiation beam having a finite dimension other than zero in the z direction as well as in a direction perpendicular thereto (that is, in a plane perpendicular to the axis of rotation 14). As will be described in detail hereinafter, the radiation beam 4 may be composed of a plurality of radiation cones that are mutually offset in the direction of the axis of rotation.

The radiation beam 4 enters an examination zone 13 in which an object may be present, for example a patient on a patient table (both of which are not shown). The examination zone 13 is shaped as a cylinder. After having traversed the examination zone 13, the X-ray beam 14 is incident on a two-dimensional detector unit 16 connected to the gantry 1.

The detector unit 16 consists of a plurality of segments which are arranged at a distance from one another; however, this is not shown in FIG. 1. The detector unit describes an arc of a circle around the radiation source S in a plane perpendicular to the axis of rotation 14. However, it may also have a different shape; for example, it may describe an arc of a circle around the axis of rotation 14 or be rectilinear. Each detector segment includes a plurality of detector elements which deliver a measuring value for a ray of the radiation beam 4 in each position of the radiation source. These measuring values are also referred to as CT data hereinafter. The measuring values or CT data acquired by the detector unit 16 are applied to an image processing computer 10 which reconstructs the absorption distribution in a part of the examination zone therefrom, for example, in order to display it on a monitor 11.

The angle of aperture of the radiation beam 4 which is denoted by the reference $\alpha_{max}$ (the angle of aperture is to be understood to mean the angle enclosed by a ray of the beam 4 which is situated at the edge in a plane perpendicular to the axis of rotation 14 relative to the plane defined by the radiation source S and the axis of rotation 14) then determines the diameter of the cylindrical examination zone 13 in which the object to be examined is present during the acquisition of the CT data.

The examination zone 13, or the object or the patient table, can be displaced parallel to the axis of rotation 14 or parallel to the z axis by means of a motor 5. However, the gantry could also be displaced in this direction for this purpose. Only the relative motion is of importance during the rotation of the radiation source about the examination zone as well as during the displacement of the examination zone relative to the gantry 1; for example, instead of the patient table the gantry could be displaced in the opposite direction. When the motors 5 and 2 run simultaneously, the radiation source S and the detector unit 16 describe a trajectory in the form of a helix relative to the examination zone 13. However, if the motor 5 for the displacement in the z direction stands still and the motor 2 rotates the gantry 1, a circular trajectory is obtained for the radiation source S and the detector unit 16 relative to the examination zone 13.

The two motors 2 and 5, the image processing computer 10 the radiation source S and the transfer of the CT data from the detector unit 16 to the image processing computer 10 are controlled by a control unit.

FIG. 2 is a purely diagrammatic view of the arrangement in a plane perpendicular to the axis of rotation. The previously mentioned helix then becomes a circle 17 and the axis of rotation 14 becomes a point which is the center point of this circle. The radiation beam 4 emitted by the radiation source S traverses inter alia a diaphragm device 30, accommodated in the housing of the collimator device 3, before it enters the examination zone 13. A changing device 31, controlled by the control unit 7 (FIG. 1), makes it possible to move the various components in the housing of the collimator arrangement 3 out of the beam path when necessary.

FIG. 3 shows the geometrical relations in a first embodiment of the invention; like in the further drawings, the dimensions in the direction of the axis of rotation are shown at an enlarged scale in comparison with the dimensions in the directions perpendicular thereto. The Figure shows the trajectory which is described by the radiation source and the examination zone relative to one another and which is shaped as a helix 17. Neighboring turns of the helix 17 are situated at a distance p from one another. Also shown is the position of the radiation source S on the helix at a given instant and also the two surfaces on the helix onto which the radiation source S projects the two detector segments 161 and 162 constituting the detector unit 16 in this first embodiment. It appears that the edges of the detector segments (161 and 162 or their projections onto the helix 17) that are mutually offset in the axial direction fill exactly the intermediate space between two neighboring turns of the helix while a distance p remains between the lower edge of the upper detector segment 162 and the upper edge of the lower detector segment 161 (corresponding to the distance between two neighboring turns of the helix). The radiation source S is situated halfway therebetween.

FIG. 4 shows a development of the detector unit 16 which is composed of the two detector segments 161 and 162, the projection of the helix 17 (onto the detector unit 16 by the radiation source S) being denoted by dashed lines.

It appears that the detector segments 161 and 162 define a rectangle which, as opposed to FIG. 3, is not identical to the parallelogram-like area defined by the projection of the helix. The detector segments (with detector elements that are arranged in rows and columns in the form of a matrix are not shown in FIG. 4) can in this case be more simply constructed, because it is merely necessary to ensure that the measuring values from detector elements whose projection is situated outside the relevant segment of the helix are not taken into account for the reconstruction, redundant CT data thus being avoided.

A clearance 18 whose width (or its dimensions in the axial direction) is smaller than the width of a detector segment 161 or 162 remains between the two detector segments. The clearance 18, however, suffices to accommodate the electronic circuitry required for the detector segments or to accommodate fixing points for the detector segments or for anti-scatter grids (not shown in the drawing) which are present between the detector unit 16 and the examination zone 13 and attenuate the scattered radiation from the examination zone to a high degree.

FIG. 5 shows a diaphragm device 30 which is compatible with FIG. 4 and is accommodated in the housing of the collimator device 3 for medical examinations, the diaphragm device being made of a material which is practically impervious to X-rays. The diaphragm device includes two slits 31 and 32 which are offset relative to one another in the axial direction and via which the X-rays are incident on the detector segments 161 and 162. The slits 31 and 32 are shaped in such a manner that their projection coincides with a respective turn of the helix in the ideal case. It is thus ensured that the areas of the detector segments 161 and 162 whose CT data are not required for the reconstruction, or are to be suppressed, are not exposed to X-rays. Consequently, the radiation load also remains small.

The diaphragm forms as many radiation cones as there are detector segments, being two in the present case. A space which is free from radiation remains between every two such radiation beams. In the context of the invention a radiation beam that is composed of a plurality of such radiation cones which extend at a distance from one another is also considered to be a conical radiation beam.

Reconstruction is performed in conformity with the method disclosed in U.S. application Ser. No. 09/368 850 or in the corresponding DE-A 198 35 296. Whereas according to this method an angular range of from −270° to +270° is completely used during filtering as well as during the backprojection of the filtered data, in conformity with the present invention the CT data is set to zero for the angular range of from −90° to +90° and the CT data for the angular ranges from −270° to −90° and from +90° to +270° enters the reconstruction with a weight that has been increased 1.5 times.

FIG. 6 shows the geometrical relations in a preferred embodiment. The detector unit therein consists of three detector segments 161, 160 and 162 whose projections cover each time the clearance between two neighboring turns of the helix 17. Between the central detector segment 160 on the one side and the lower detector segment 161 or the upper detector segment 162 on the other side there remains an intermediate space whose width is exactly equal to that of the individual detector segments. Thus, a detector unit is concerned whose overall dimensions in the axial direction amount to 5 p and is composed of three detector segments of the width p, said segments being arranged at a distance p from one another. As has been described with reference to FIG. 4, the development of the individual detector segments may again have the shape of a rectangle.

The advantage of this embodiment resides in the fact that the plane which extends perpendicularly to the axis of rotation 14 and in which the radiation source S is situated intersects the central detector segment 160. Consequently, this central detector segment can be used for the acquisition of CT data when the examination zone is scanned along a circular trajectory instead of a helical trajectory.

FIG. 7 is a sectional view in a plane which contains the axis of rotation of the arrangement shown in principle in FIG. 6. The helix is not shown in this case. It appears that each of the detector segments 160, 161 and 162 consists of two parts 160*a* and 160*b*, 161*a* and 161*b*, and 162*a* and 162*b*, respectively. These parts are joined in such a manner that the radiation-sensitive areas with the individual detector elements directly adjoin one another whereas the electronic circuitry for processing the signals of the detector elements is situated at the edges of the parts that are remote from one another (for example, 160*a*, 160*b*).

An anti-scatter grid 18 is arranged in front of each detector segment. This grid includes lamellae that extend perpendicularly to the plane of drawing of FIG. 7 and are aligned relative to the radiation source and attenuate scattered radiation which is generated in the examination zone and is incident on the anti-scatter grid 18 at an angle other than that at which the radiation emitted by the radiation source is incident. The clearance between two detector segments can be used not only for accommodating the electronic circuitry but also for stable fixation (not shown) of the anti-scatter grids and the detector segments to the gantry.

The fact that a complete CT image can be reconstructed by means of the CT data of the central detector segment on the one hand and the CT data of the two outer detector segments on the other hand can be utilized for computed tomography "dual energy" examinations. The two outer detector segments 161 and 162 are then exposed to radiation of an energy which is different than that whereto the central detector segment is exposed. To this end, the collimator device is provided with a filter 40 (see FIG. 2) which hardens the radiation to a different extent. For example, the filter may be constructed in such a manner that the radiation to the central detector segment remains fully unaffected (that is, in this region the filter is provided with an aperture which allows unimpeded passage to the radiation), whereas the radiation to the two outer detector segments is hardened in a given manner by means of an appropriate filter material of a suitable thickness. The advantage of such a "dual energy" examination in conjunction with the invention consists in that the CT data required for this purpose can be simultaneously (instead of successively) acquired.

FIGS. 8*a* and 8*b* show two different embodiments in which the projection of the outer edges of the detector unit covers a path amounting to 7 p. The detector unit again consists of three detector segments, that is, a central detector segment 160 and two equally wide outer segments 161 and 162.

However, whereas in the embodiment shown in FIG. 8*a* the central detector segment (in the projection) has only the width p and each of the outer detector segments has the width 2 p, the central detector segment of the embodiment shown in FIG. 8*b* has the width 3 p and the two outer detector segments 161 and 612 have the width p. This embodiment is better suitable for examinations involving a circular trajectory.

The projection of the outer edges of the detector unit may also cover more than 7 p (generally (2n+1)p, where n is an integer) and the detector unit may be subdivided into up to n+1 detector segments. The detector segments should then be symmetrically arranged with respect to the radiation source S (that is, their focus wherefrom the radiation emanates) or relative to the point in which the perpendicular from S to the axis of rotation 14 punctures the cylinder defined by the helix.

What is claimed is:

1. A computed tomography apparatus which includes a scanning unit which includes a radiation source (S) and a detector unit (16) which is connected thereto in order to detect a conical radiation beam, emitted by the radiation source, after its passage through an examination zone (13) or an object present therein, a drive device (2, 5) for realizing a relative motion in the form of a helix, comprising a rotation about an axis of rotation (14) and a displacement parallel to the axis of rotation, between the scanning unit (S, 16) and the examination zone (13) or the object, the projection of the outer edges of the detector unit, being mutually offset in the axial direction, onto the helix including a path of (2n+1)p, where n is an integer >1 and p corresponds to the axial offset of two neighboring turns of the helix, and the detector unit including a plurality of detector segments that are spatially separated from one another and are mutually offset in the axial direction, each of said detector segments being arranged and shaped in such a manner that its projection onto the helix covers at least two neighboring turns of the helix.

2. A computed tomography apparatus as claimed in claim 1, characterized in that n=1 and that the detector unit includes two detector segments that are situated to both sides of a plane that extends perpendicularly to the axis of rotation and contains the radiation source.

3. A computed tomography apparatus as claimed in claim 1, characterized in that n amounts to at least 2 and that the detector unit includes at least three detector segments, one of which is situated in a plane that extends perpendicularly to the axis of rotation and contains the radiation source whereas a respective half of the remaining segments is situated to each side of this plane.

4. A computed tomography apparatus as claimed in claim 1, characterized in that a diaphragm device is arranged between the radiation source and the examination zone in such a manner that it shields the clearances between the detector segments from the radiation from the radiation source.

5. A computed tomography apparatus as claimed in claim 3, characterized in that between the radiation source and the examination zone there is arranged a filter device whose absorption properties exhibit such a spatial dependency so as to generate radiation of two different energy spectra in axially offset areas such that a first group of detector segments receives radiation having a first energy spectrum whereas a second group of detector segments receives radiation having a second energy spectrum.

6. A detector unit for a computed tomography apparatus which includes:

a scanning unit which includes a radiation source (S) that can be mechanically connected to the detector unit and serves to produce a conical radiation beam emitted by the radiation source, a drive device (2, 5) for realizing a relative motion in the form of a helix, comprising a rotation about an axis of rotation (14) and a displacement parallel to the axis of rotation, between the scanning unit (S, 16) and the examination zone (13) or the object, the projection of the outer edges of the detector unit, being mutually offset in the axial direction, onto the helix including a path of (2n+1)p, where n is an integer >1 and p corresponds to the axial offset of two neighboring turns of the helix, and the detector unit including a plurality of detector segments that are spatially separated from one another and are mutually offset in the axial direction, each of said detector segments being arranged and shaped in such a manner that its projection onto the helix covers at least two neighboring turns of the helix.

* * * * *